United States Patent
Breeuwer

(10) Patent No.: US 7,047,061 B2
(45) Date of Patent: May 16, 2006

(54) METHOD OF LOCALIZING THE MYOCARDIUM OF THE HEART AND METHOD OF DETERMINING PERFUSION PARAMETERS THEREOF

(75) Inventor: Marcel Breeuwer, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 371 days.

(21) Appl. No.: 10/012,024

(22) Filed: Dec. 5, 2001

(65) Prior Publication Data

US 2002/0087072 A1    Jul. 4, 2002

(30) Foreign Application Priority Data

Dec. 5, 2000   (EP) .................................. 00204343

(51) Int. Cl.
*A61B 5/055* (2006.01)
(52) U.S. Cl. ...................... 600/410; 600/419; 600/420; 382/131
(58) Field of Classification Search ................ 600/410, 600/420, 419; 324/306, 309, 307; 382/128, 382/266, 131; 128/920, 922
See application file for complete search history.

(56) References Cited

U.S. PATENT DOCUMENTS 5,669,382 A * 9/1997 Curwen et al. ............. 600/425
5,797,396 A * 8/1998 Geiser et al. ............... 600/407

FOREIGN PATENT DOCUMENTS

WO   WO9318470   9/1993

OTHER PUBLICATIONS

Waiter et al. "Determination of Normal Regional Left Ventricular Function from Cine-MR Images using a Semi-Automated Edge Detection Method" 1999, Magnetic Resonance Imaging, vol. 17, No. 1, pp. -99-107.*

* cited by examiner

*Primary Examiner*—Ruth S. Smith

(57) ABSTRACT

The invention relates to a method of deriving the myocardial region from one or more MR images. Left and right ventricle contours (1, 2) are determined. The thickness or width (D) of the myocardial region is computed from the distance between these contours in a predetermined part (A) of the image (images). The location of the myocardial region outside the preset region is derived on the basis of this distance.

8 Claims, 2 Drawing Sheets

METHOD OF LOCALIZING THE MYOCARDIUM OF THE HEART AND METHOD OF DETERMINING PERFUSION PARAMETERS THEREOF

BACKGROUND OF THE INVENTION

The invention relates first of all to a method of determining a position of the myocardium of the heart from an image or a series of images of the heart of a patient as acquired, for example, by means of the MR measuring technique.

A method of this kind is known, for example, from WO-A-93/18470 (PCT/US92/08497). Such a method makes it possible to carry out perfusion studies of the heart.

In conformity with a further aspect of the invention, the invention also relates to a method of determining, for example, while utilizing MR images, perfusion parameters of the heart of a patient while administering a contrast liquid, that is, notably a method of determining perfusion parameters of the myocardium of the heart.

From WO-A-93/18470 it is known to derive an image of a heart being examined from images acquired by means of nuclear radiation; therein, intensity patterns in the image are related to one another so as to determine the organ contours.

BRIEF SUMMARY OF THE INVENTION

It is an object of the invention to enhance this method such that the perfusion parameters of the heart being examined can be determined without human intervention.

A first problem to be solved in this respect is the determination of the position of the myocardium of the heart. In accordance with the invention this problem is solved in that a left ventricle contour and a right ventricle contour of the heart are determined, that a thickness measure of the myocardium is derived from the distance of said contours in a predetermined region in which both contours of the ventricles extend, and that outside said region the position of the myocardium is bounded by the left ventricle contour and an outer contour that extends outside the left ventricle contour at a distance that is equal to the thickness measure. The left ventricle contour then corresponds to the so-called endocontour of the left ventricle whereas the outer contour corresponds to the so-called epicontour of the left ventricle.

In order to realize a reliable representation of the situation of the myocardium it is desirable to determine the thickness measure of the myocardium by selection of the largest distance or the mean distance between the left ventricle contour and the right ventricle contour in the predetermined region.

In order to enhance the reliability of the localization of the myocardium even further, the thickness measure is preferably determined by multiplying the distance between the two contours by a predetermined factor that is greater than one.

The determination of the thickness of the myocardium can be reliably performed notably in that the predetermined region in which both contours of the ventricles extend is bounded by two tangent lines that, in distinct locations, partly coincide with or are tangent to the right ventricle contour and intersect one another at a center of gravity of the left ventricle.

Using the situation of the myocardium as determined in the described manner, in conformity with a further aspect of the invention the perfusion parameters of the heart examined can be determined efficiently and without human intervention, that is, notably the perfusion parameters of the myocardium of the heart.

To this end, a contrast liquid is administered to the patient whose heart is being examined, the image formed of the myocardium is segmented and at a time intensity curve that represents the variation in time of the concentration of the contrast liquid in the myocardium is determined for at least one segment, after which the perfusion parameters are derived from the time intensity curve.

In a first version of such a method the at least one segment whose time intensity curve is determined is a predetermined position in the myocardium. The perfusion behavior of said position in the myocardium can thus be effectively determined.

A further suitable version of the method in accordance with the invention is characterized in that the myocardium is segmented by way of lines of intersection through the left ventricle contour and the outer contour that originate from the center of gravity of the left ventricle. The perfusion behavior of the segments thus formed can subsequently be recorded.

The method can be very advantageously executed in such a manner that at least two lines of intersection that segment the myocardium are formed by the tangent lines that bound the region in which the left ventricle contour and the right ventricle contour extend at some distance from one another.

The method in accordance with the invention can be suitably executed without human intervention in a computer-controlled application. In order to limit the computing capacity required and to achieve fast processing of the measuring data it is then desirable to define a time window that is bounded by a starting time $T_B$ and a finishing time $T_E$ for the analysis of the variation of the time intensity curve; to this end, for the left ventricle of the heart an instant $T_{LV}$ is determined at which a maximum is reached in the variation of the time intensity curve of the left ventricle and the starting time $T_B$ is determined to be the instant at which the time intensity curve of the left ventricle reaches a predetermined fraction of said maximum, where $T_B$ is smaller than $T_{LV}$, and the finishing time $T_E$ is derived from the variation of the time intensity curve of the myocardium by adding a predetermined time delay W to the instant $T_{MYO}$ at which this curve reaches a maximum value.

The invention also relates to a data processing system. The data processing system of the invention is arranged to carry out the method of the invention.

The invention also relates to a computer program. The computer program according to the invention can be loaded into the working memory of a data processing system, so that the data processing system can carry out the method of the invention.

Preferably, the computer program of the invention may be made available from a data carrier, such as a CD Rom disk. The computer program may also be downloaded from a data network such as the 'world-wide web'.

BRIEF DESCRIPTION OF THE DRAWING FIGURES.

The invention will be described in detail hereinafter with reference to the accompanying drawing.

DETAILED DESCRIPTION OF THE INVENTION

Figure 1:
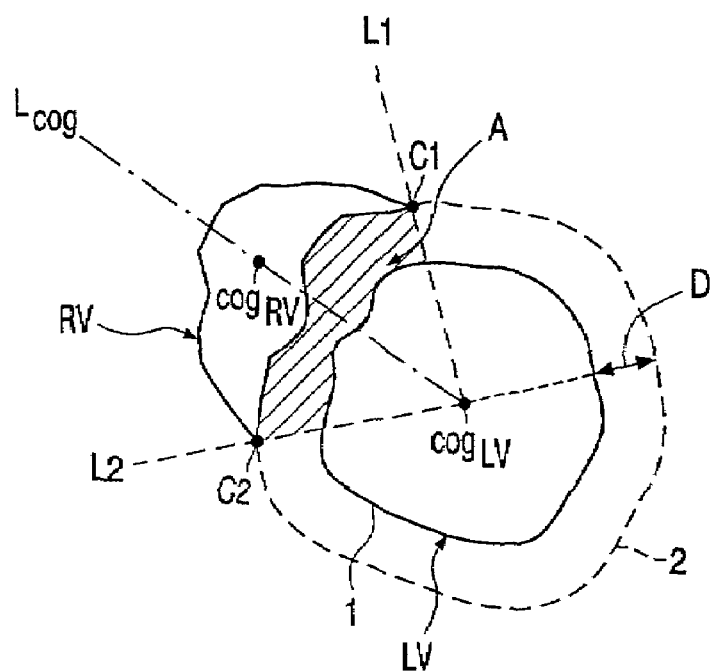
FIG. 1 is a diagrammatic representation of a heart that is being studied and for which the situation of the myocardium is determined.

FIG. 1 is a diagrammatic representation of a heart with a left ventricle $L_V$ and a right ventricle RV. The method in accordance with the invention is intended to determine the position of the myocardium that is bounded by the endocardium formed by the left ventricle contour 1 and the outer contour 2 of the myocardium that is also referred to as epicardium. In conformity with the method in accordance with the invention, for example, first the center of gravity $COG_{LV}$ of the left ventricle can be determined and also the center of gravity $COG_{RV}$ of the right ventricle $R_V$. A line $L_{COG}$ can be plotted through the centers of gravity $COG_{LV}$ and $COG_{RV}$, said line subsequently being rotated around the center of gravity $COG_{LV}$, of the left ventricle. Such a rotation of the line $L_{COG}$ produces a tangent line L1 and a tangent line L2 in two positions of the right ventricle contour. These two tangent lines L1 and L2 bound a region in which the right ventricle contour and the left ventricle contour extend at some distance from one another and bound the myocardium. This region is represented by shading in the Figure and is denoted by the arrow A. In conformity with the method in accordance with the invention the region A is subsequently used to derive a thickness measure for the myocardium. This operation may be based either on the largest distance or on the mean distance between the left ventricle contour and the right ventricle contour in the region A. The thickness measure D thus determined is subsequently used to define an outer contour 2 at some distance from the left ventricle contour 1, that is, in as far as it is situated outside the region A. For the determination of the thickness measure D a multiplication factor of a value greater than 1 may also be applied, if necessary, to the previously mentioned distance between the left ventricle contour and the right ventricle contour in the region A.

Figure 2:
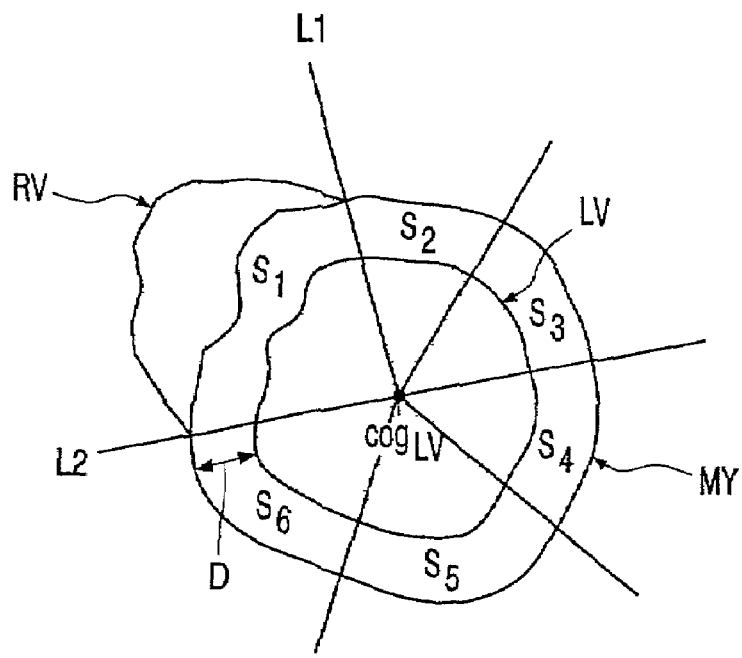
FIG. 2 illustrates a feasible segmentation of the myocardium.

FIG. 2 shows the same heart with the right ventricle RV, the left ventricle LV and the myocardium MY of a thickness D determined as described above. The Figure also shows the center of gravity $COG_{LV}$ of the left ventricle. Furthermore, the Figure shows a segmentation of the myocardium MY in the form of a so-called spoke wheel; at least two lines of the spoke wheel may coincide with the tangent lines L1 and L2 of FIG. 1. The lines of intersection L1 and L2 thus define a segment $S_1$. The further segments $S_2$ to $S_6$ can be adjusted at random or be chosen such that the various segments occupy the same surface area. It is also possible to choose each time the same angle between the various lines of intersection that constitute the spoke wheel.

Another possibility (not shown in the Figures) consists in performing the segmentation in such a manner that a single image point or group of coherent image points is selected. The further analysis of the perfusion parameters, notably perfusion parameters of the myocardium of the heart, can be performed on the segmented image thus obtained. It is common practice that the images are acquired by means of an MR scanning technique and that a contrast liquid has been administered to the patient whose heart is being examined. Subsequently, the segmented image can be further processed by determining a time intensity curve thereof.

For such a time intensity curve the time is plotted on the X axis and the (mean) intensity of the image points (gray values) measured by means of the MR scanning technique is plotted on the Y axis.

Figure 3:
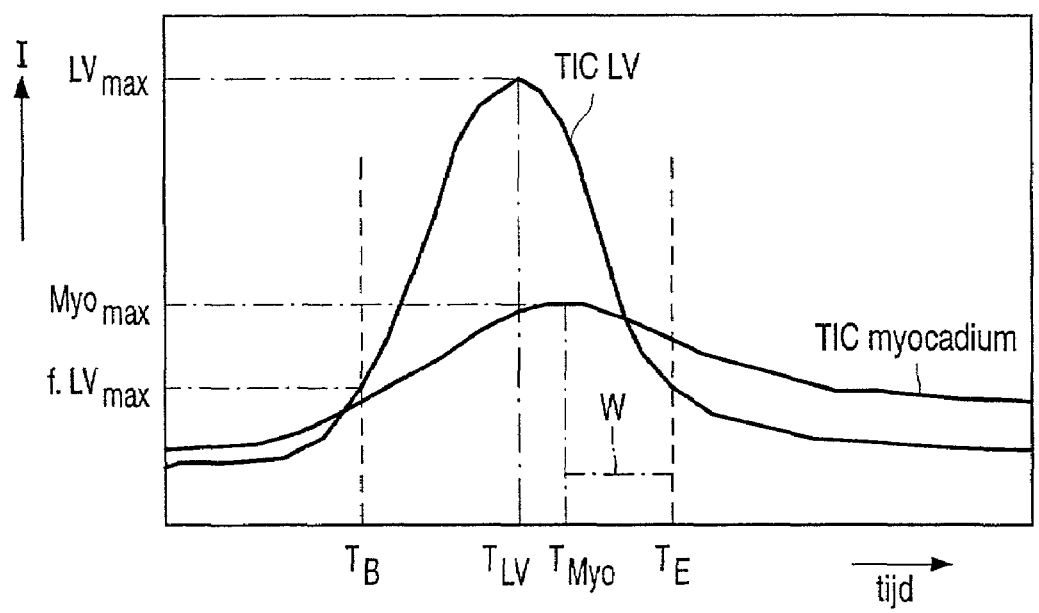
FIG. 3 shows a typical variation of the time intensity curves of the myocardium and the left ventricle.

FIG. 3 shows an example of such curves. This Figure shows the graph of two time intensity curves, that is, the mean time intensity curve $TIC_{LV}$ of the left ventricle LV and the mean time intensity curve TIC myocardium of the myocardium. The perfusion measurement is performed on the basis of these time intensity curves, that is, preferably in such a manner that the analysis is performed on the basis of a time window that is involved in the evaluation and is bounded by a starting time $T_B$ and a finishing time $T_E$, the starting time $T_B$ and the finishing time $T_E$ being determined as follows.

The maximum $LV_{MAX}$ of the TIC of the LV is determined and also the instant in time $T_{LV}$ at which this maximum occurs.

The beginning $T_B$ of the analysis window is positioned at that instant in time for which it holds that $T_B < T_{LV}$ and for which it also holds that the time intensity curve of the left ventricle LV lies for the first time at or below a fraction f (f<1.0, for example f=0.15) of the maximum value $LV_{MAX}$. It may be decided, if desired, to position $T_B$ at a fixed distance in time ahead of the instant at which the value of the time intensity curve is less than $f.LV_{MAX}$.

The maximum $MYO_{MAX}$ of the time intensity curve of the myocardium is subsequently determined, and also the instant $T_{MYO}$ at which this maximum occurs.

The finishing moment $T_E$ of the analysis window is positioned fixed amount W later than the instant at which the time intensity curve of the myocardium is maximum, that is, $T_E = T_{MYO} + W$.

After the time window $T_B - T_E$ has been determined in the indicated manner, a mean time intensity curve can be determined for each segment in the spoke wheel or for each desired image point separately. Subsequently, the desired perfusion parameters can be derived therefrom, for example, the "mean upslope", the "maximum upslope", and the "time-to-peak". These terms are well known to those skilled in the art so that they need not be further elaborated herein.

Figure 4:
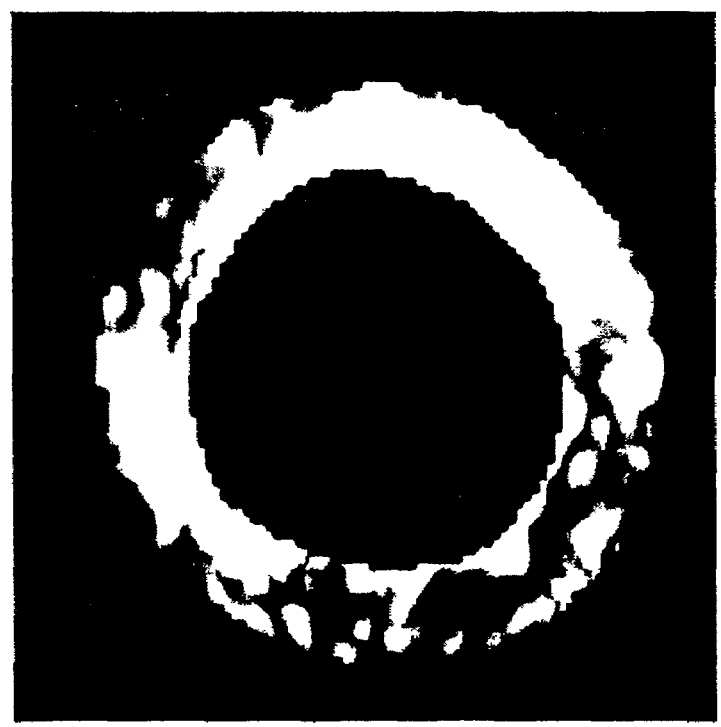
FIG. 4 shows a feasible presentation of given perfusion parameters relating to the heart being studied.

Finally, FIG. 4 shows the monitor image that can be obtained in the case of display of a parameter that determines perfusion in relation to the myocardium and has been determined for a number of points of this myocardium. The Figure shows the so-called maximum upslope. The white regions represent good perfusion; the black regions represent poor perfusion.

What is claimed is:

1. A method of determining a position of the myocardium of the heart from a magnetic resonance (MR) image or a series of MR images of the heart of a patient, comprising the steps of:
    first determining from the image or images a left ventricle contour and a right ventricle contour of the heart;
    second determining a thickness measure of the myocardium based on a detected distance between said contours in a predetermined region in which both contours of the left and right ventricles extend such that outside said region the position of the myocardium is bounded by said left ventricle contour and an outer contour that extends outside said left ventricle contour at a distance that is equal to the thickness measure of the myocardium.

2. A method as set forth in claim 1, wherein the step of second determining includes that the thickness measure of the myocardium is determined by selection of the largest distance, or the mean distance, between said left ventricle contour and said right ventricle contour in the predetermined region.

3. A method as set forth in claim 1, wherein the step of second determining includes that the predetermined region in which said left ventricle and right ventricle contours extend is bounded by two tangent lines disposed at distinct locations which partly coincide with, or are tangent to, said right ventricle contour and which intersect one another at a center of gravity of the left ventricle.

4. A method as set forth in claim 3, wherein the step of second determining includes that at least two lines of intersection that segment the myocardium are formed by the tangent lines that bound the region in which the left ventricle contour and the right ventricle contour extend at some distance from one another.

5. A magnetic resonance (MR) method for determining perfusion parameters of the heart of a patient while administering a contrast liquid, comprising the steps of:
  first calculating a position of the myocardium of the heart from a magnetic resonance (MR) image or a series of MR images of the heart of a patient, which step of calculating further comprises the steps of:
    first determining from the image or images a left ventricle contour and a right ventricle contour of the heart,
    second determining a thickness measure of the myocardium based on a detected distance between said contours in a predetermined region in which both contours of the left and right ventricles extend such that outside the region the position of the myocardium is bound by the left ventricle contour and an outer contour that extends outside the left ventricle contour at a distance that is equal to the thickness measure of the myocardium;
  segmenting the myocardium;
  second calculating a time intensity curve that represents the variation in time of the concentration of the contrast liquid in the myocardium for at least one segment; and
  deriving the perfusion parameters from the time intensity curve.

6. A method as set forth in claim 5, wherein the step of second calculating includes determining that the at least one segment whose time intensity curve is determined is a predetermined position in the myocardium.

7. A method as set forth in claim 5, wherein the step of segmenting includes generating lines of intersection through the left ventricle contour and the outer contour that originates from the center of gravity of the left ventricle.

8. A method as set forth in claim 5, wherein the step of second calculating includes further determining a time window bound by a starting time $T_B$ and a finishing time $T_E$ for the analysis of the variation of the time intensity curve, that for the left ventricle an instant $T_{LV}$ is determined at which a maximum is reached in the variation of a time intensity curve of the left ventricle, that the starting time $T_B$ is determined to be the instant at which the time intensity curve of the left ventricle reaches a predetermined fraction of said maximum, where $T_B$ is smaller than $T_{LV}$, and that the finishing time $T_E$ is derived from the variation of the time intensity curve of the myocardium by adding a predetermined time delay W to the instant $T_{MYO}$ at which this curve reaches a maximum value.

* * * * *